United States Patent [19]

Jacke

[11] Patent Number: 4,521,520
[45] Date of Patent: Jun. 4, 1985

[54] METHOD FOR IN HOUSE OCCULT BLOOD TESTING

[75] Inventor: Stanley E. Jacke, Malvern, Pa.

[73] Assignee: SmithKline Diagnostics, Inc., Sunnyvale, Calif.

[21] Appl. No.: 483,083

[22] Filed: Apr. 7, 1983

[51] Int. Cl.³ .................. A61B 5/00; G01N 33/50
[52] U.S. Cl. ........................ 436/66; 4/144.2; 4/315; 4/661; 422/56; 422/61
[58] Field of Search .............. 422/55, 56, 57, 58, 422/61; 436/66; 4/315, 661, 141.2; 128/759

[56] References Cited

U.S. PATENT DOCUMENTS

| | | | |
|---|---|---|---|
| 2,840,826 | 7/1958 | Ebbesen et al. | 4/661 |
| 3,012,976 | 12/1961 | Adams et al. | 422/56 X |
| 3,346,883 | 10/1967 | Ersek | 4/315 X |
| 3,718,431 | 2/1973 | Wild | 436/66 |
| 3,996,006 | 12/1976 | Pagano | 422/58 X |
| 4,175,923 | 11/1979 | Friend | 422/56 X |
| 4,225,557 | 9/1980 | Hartl et al. | 422/56 |
| 4,259,964 | 4/1981 | Levine | 128/759 X |
| 4,445,235 | 5/1984 | Slover et al. | 4/144.2 |

*Primary Examiner*—Barry S. Richman
*Assistant Examiner*—Robert J. Hill, Jr.
*Attorney, Agent, or Firm*—Joseph A. Marlino; Stuart R. Suter; Alan D. Lourie

[57] ABSTRACT

A method for determining the presence of occult blood in the bowl of a toilet includes the steps of suspending from the seat of the toilet an absorbent test sheet carrying a test reagent, defecating onto said sheet, flipping said sheet over to deposit the fecal matter in the bowl water, applying a developing solution to said sheet and observing whether a portion of said sheet is dyed blue. Preferably the test sheet is an absorbent paper printed or impregnated with guaiac.

7 Claims, 6 Drawing Figures

U.S. Patent  Jun. 4, 1985  Sheet 1 of 3  4,521,520
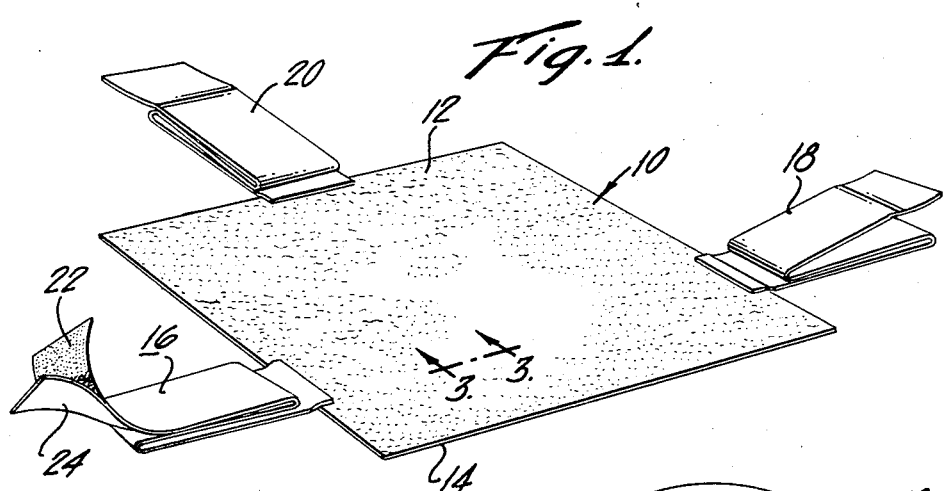
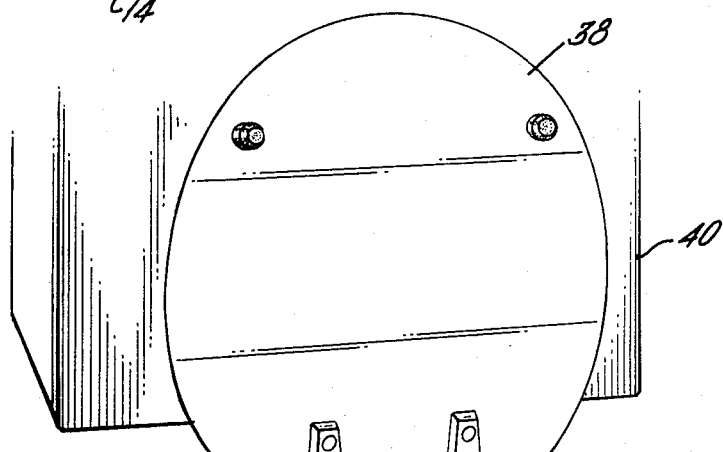
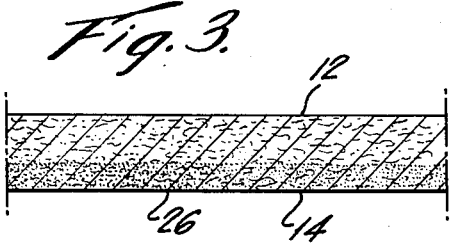
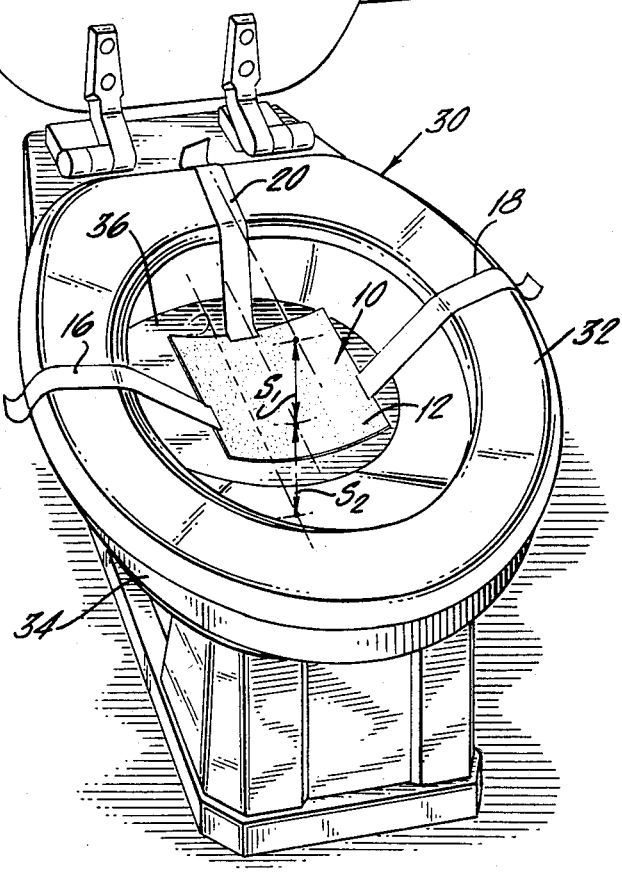

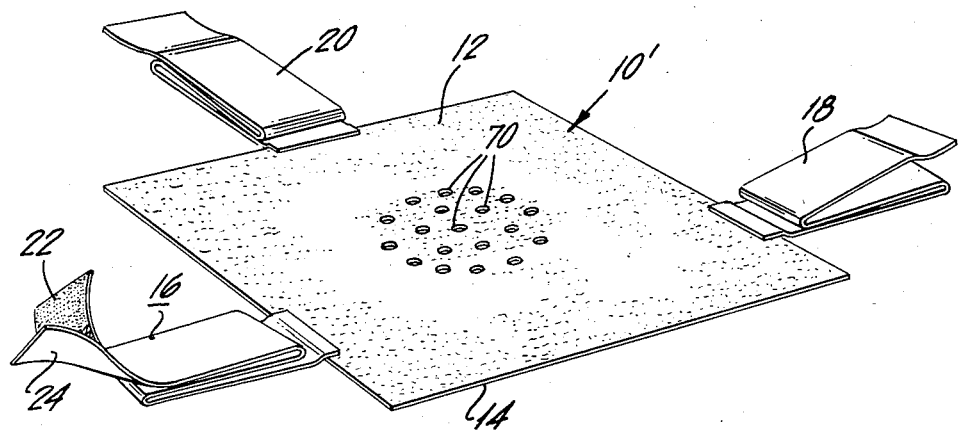

METHOD FOR IN HOUSE OCCULT BLOOD TESTING

The present invention relates to a method for detecting the presence of occult blood in fecal matter, particularly to a method for detecting the presence of fecal occult blood in the privacy of a person's home.

BACKGROUND OF THE INVENTION

Colorectal cancer in man is frequently asymptomatic requiring special efforts to be detected, particularly in its early stages. Contamination of the stools with occult blood occurs before visible bloody stools are detected. The early diagnosis of carcinomas of the colon and rectum is therefore aided by the detection of occult blood in the stool.

Procedures for testing for the presence of occult blood in the fecal matter are well known. For example, tests employing specimen slides such as those described in U.S. Pat. No. 3,996,006 are well recognized in the medical art as practicable and rational screening tests for the early detection of colorectal cancer. Briefly, the test consists of using a specimen test slide which employs an absorbent sheet treated with a reagent which gives a color reaction when contacted with blood. The sheet of absorbent paper is sandwiched between a front and rear panel. The front panel has a plurality of openings and a cover for said openings. The rear panel has tab means opposite said openings. An example of such slides are those sold under the trademark of 'Hemoccult'.

To use the above noted commercial slides the patient must obtain specimens from different parts of his stool and smear them on the absorbent paper through the openings in the front panel. These feces samples must be removed from a toilet bowl or bed pan on a wooden spatula and then smeared on the absorbent sheet. The tab or flap in the rear panel is opened and a developing solution is applied to the absorbent paper opposite the openings in the front panel. A blue color denotes a positive test, i.e., presence of occult blood in the fecal matter. Because of the inhomogeneity of feces and because gastrointestinal bleeding tends to be intermittent, investigations have shown that a multiplicity of specimens should be tested for optimum results. A random single portion from a stool is not sufficient because the occult blood may be in a portion of the stool not tested. The patient is therefore given slides with, for example, six test sites and instructed to make smears with two separate portions of his stool on three separate days.

Although this test has been well accepted by medical experts as a screening approach for colorectal cancer, it does have several major disadvantages. The test is normally conducted in a physician's office or at a diagnostic laboratory. However, many patients are requested to initiate the test at home and then send the slide to a physician or laboratory for completion and analysis.

One disadvantage is that the patient is faced with the difficult task of making smears from separate portions of his stool. The extreme unpleasantness, inconvenience and difficulty of the test confronting the patient cannot be overstated. Most patients are unaccustomed to handling their stool, particularly when the stool is in a toilet bowl under perhaps six inches of water. Needless to say, many patients become nauseous at the thought of conducting such a test. A further disadvantage is that when the patient initiates the test at home, he must store the fecal specimens of the first two days until he takes his last specimen on the third day. The patient is cautioned to protect the slides from light and heat. The only cool spot available to the average patient would be his refrigerator. It is appparent he would not wish to store his fecal specimens in the family refrigerator.

SUMMARY OF THE INVENTION

It is therefore an object of this invention to provide a simple, rapid, clean and convenient method of detecting fecal occult blood which does not require the patient to handle his fecal matter either during or after the test.

It is a further object of this invention to provide a simple method for testing occult blood which can be carried out by the average patient in the privacy of his home and therefore assist in the early diagnosis of colorectal cancer.

It is a still further object of this invention to provide a test method for occult blood which is understood by the average patient and is easy to analyze and reproduce and does not require the services of a physician or laboratory technician.

It is yet another important object of this invention to eliminate the necessity for a patient taking multiple specimens of his stool for testing.

Briefly, the invention provides a method for determining the presence of occult blood by suspending an absorbent sheet carrying a test reagent such as guaiac below the toilet seat surface but not in the water. The sheet acts as a saddle or hammock and catches the fecal matter before it reaches the water in the toilet bowl. The fluids from the fecal matter soak the absorbent reagent impregnated sheet and any excess fluid, such as urine, drains through openings provided in the sheet. After defecating, the absorbent sheet is flipped over on its supports dumping the fecal matter in the bowl. A developing solution is then applied to the rear portion of the sheet outlined by the fecal mass. A blue color indicates the presence of occult blood. When the test is completed the supports are released from the toilet seat and the entire assembly, i.e., saddle and supports, is flushed down the toilet.

A detailed description and better understanding of this invention can be had by referring to the accompanying drawings which show a preferred embodiment of the present invention.

FIG. 1 is a perspective view showing the absorbent test sheet with supports attached thereto.

FIG. 2 is a perspective view of a conventional toilet showing the absorbent sheet positioned prior to use.

FIG. 3 is a greatly enlarged schematic, fragmentary sectional view taken on line 3,3 of FIG. 1 showing the guaiac reagent.

FIG. 6 is a perspective view similar to FIG. 1 showing openings in the test sheet to permit drainage of excess fluid.

Figure 4:
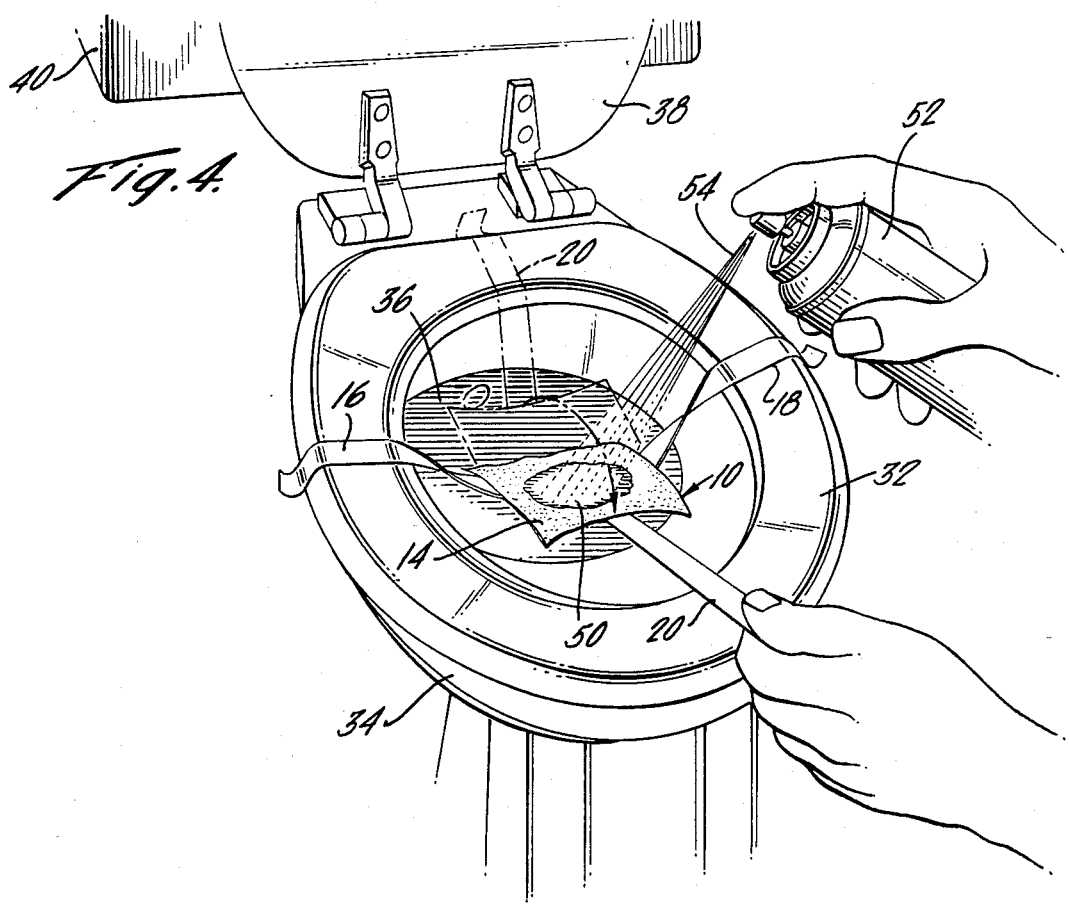
FIG. 4 is a view similar to FIG. 2 but showing the absorbent sheet repositioned after use and the stained underside having developer applied.
Figure 5:
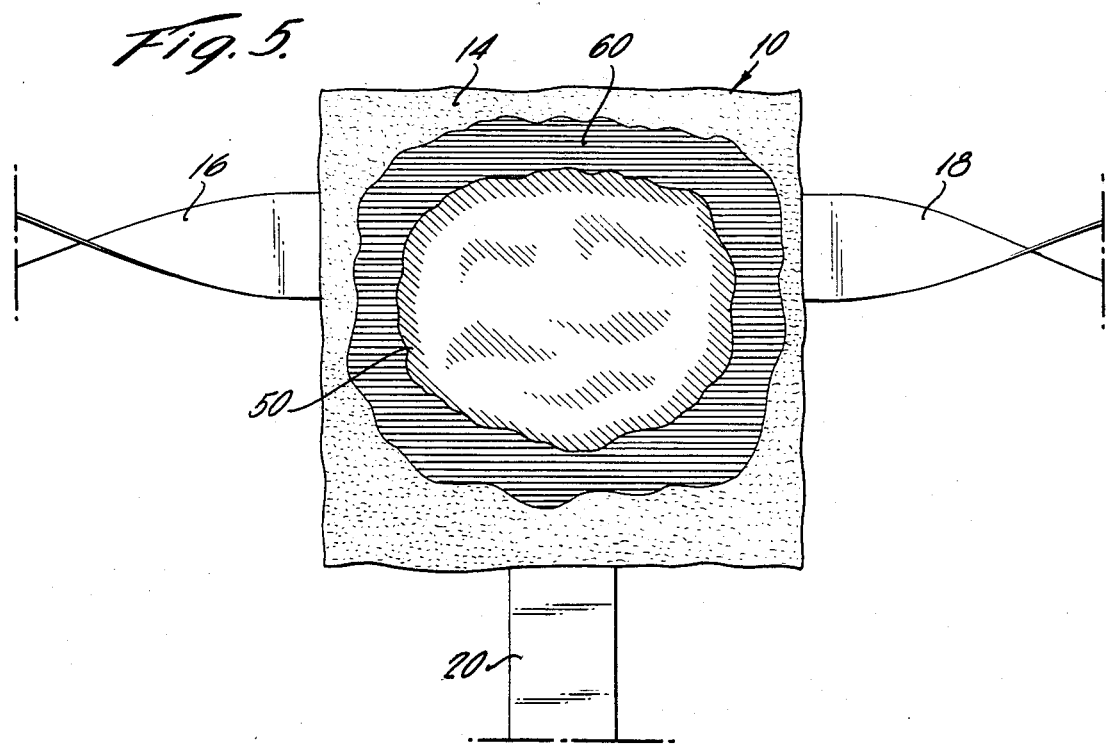
FIG. 5 is an enlarged plan view of the lower surface of the absorbent sheet shown in FIG. 4 having been sprayed with developer showning a blue color or positive test.

Referring to FIG. 1, absorbent test sheet 10 has an upper surface 12, and a lower surface 14, and supports 16, 18, and 20 having an adhesive face 22 and a strip of covering tape 24. As shown in FIG. 2, which discloses toilet 30 together with tank 40 and seat cover 38, the test sheet 10 is suspended below the toilet seat 32 mounted on bowl 34 and above the bowl water 36. The test sheet is secured to the toilet seat by supports 16, 18, and 20. The vertical distance of the test sheet below the plane of the toilet seat is represented by $S_1$ and $S_2$ represents the vertical distance of the test paper above the surface plane of the water. As illustrated in FIG. 3, a portion of the absorbent sheet may be layered with a reagent 26. The sheet may also be impregnated or printed with the reagent. FIG. 4 demonstrates the flipping of absorbent sheet 10 and application of developing solution 54 from spray can 52 to the stained 50 lower surface 14 of the sheet. FIG. 5 discloses a blue color 60 which forms on the lower surface of the absorbent sheet after application of the developing solution. This denotes a positive test. FIG. 6 demonstrates a test sheet 10' with openings 70 which permit the drainage of excess fluids such as urine.

To perform the method of this invention the patient suspends absorbent sheet 10 below toilet seat 32 by means of supports 16, 18, and 20. The sheet is suspended below the toilet seat surface and above the bowl water 36. It is important to keep the absorbent sheet dry and not let it touch the water. This assures that the blood is not diluted or dispersed by the water. It also permits direct contact between the stool and the absorbent test sheet.

In a preferred embodiment the sheet is suspended on two sides of the seat by supports 16 and 18 and on the back of the seat by support 20. After defecating, the back support 20 is separated from the toilet seat and flipped forward dumping the fecal matter into the bowl water 36 and positioning the sheet so that the lower surface 14 of asborbent sheet 10 is exposed. Developing solution is then applied to a portion of the lower stained surface. The absorbent test sheet is then observed for any color change. A blue color denotes a positive test. When the test is completed, the patient merely releases the test strip from the toilet seat and flushes it down the toilet.

The absorbent test sheet employed in this invention should be disposable and have sufficient strength to catch and hold the fecal matter. A variety of materials such as those made of carboxymethyl cellulose and polyvinyl alcohol may be employed. Preferably, absorbent paper such as Whatman #1 or similar paper is employed. The test sheet should be of such a size as to fit inside the toilet bowl and still leave space for manipulating the paper. Advantageously a sheet of from about 3 to 4 inches in diameter or square is employed.

Advantageously the absorbent test sheet may have openings to permit the drainage of urine.

The absorbent test sheet will carry a test reagent such as, for example, guaiac, o-tolidine, benzidine or other well known blood detecting reagents. Most advantageously the test sheet is impregnated or printed with guaiac.

When a developing solution is employed, it may be any well known to the art, for example, aqueous peroxide solutions.

While the preferred method of this invention involves the step of applying a developing solution to the absorbent sheet, an alternative method which eliminates this step may be employed. The development of a color could be accomplished by the placement of an organic hydroperoxide on the absorbent paper during manufacture. This can be accomplished by printing or placing the hydroperoxide in solution and impregnating the absorbent material. The absorbent material is then dried. The latter method of applying hydroperoxide to absorbent paper is well known and described in U.S. Pat. Nos. 3,012,976 and 4,063,894.

Examples of hydroperoxides which may be employed are those such as cumene hydroperoxide, diisopropylbenzene hydroperoxide, para-methane hydroperoxide and tetraline hydroperoxide. Other hydroperoxides which liberate oxygen in the presence of blood and catalyzes the oxidation of chromogen with the production of a color may also be employed. When the test sheet is thus pretreated with a hydroperoxide, the patient merely has to flip the sheet and immediately note if a color developed on the lower surface. Addition of a developing solution is not necessary in this case.

The supports for the absorbent sheet can be any releasable adhesive material such as, for example, masking tape, adhesive tape or the like.

Preferably, the method and materials are made available to a person in the form of a home test kit. The kit comprises absorbent test sheets carrying a guaiac reagent and having releasable adhesive means attached thereto to permit suspension of the sheet from a toilet seat. Additionally, the kit will comprise a receptable containing a developing solution, such as a hydroperoxide solution, which when applied to the absorbent test sheet turns the sheet blue in the presence of occult blood.

When the test method of this invention is carried out the objects set forth above are fulfilled. Further, the disadvantages noted above for the presently available commercial slides are overcome. The novel method of this invention results in a test for fecal occult blood that is sensitive, simple, rapid, clean, inexpensive and convenient. Further, this test can be performed and analyzed by an unskilled person in the privacy of his home.

A major advantage of the method of this invention is that multiple specimens of stool need not be tested. One half the stool sample comes in direct contact with the absorbent test sheet. This large area of contact between the fecal mass and test sheet gives reasonable assurance that streaks of blood in different sections of the stool will not be missed. It is easy to miss a spot of occult blood when random samples of the stool are taken with a wooden spatula.

The above embodiments are illustrative and are not intended to be limiting.

What is claimed is:

1. A method for determining the presence of occult blood in fecal matter which comprises:
    suspending, via a multi-support suspension device, an absorbent test sheet from a seat of a toilet for the reception of fecal matter, said multi-support suspension device being configured to permit on-site rotation of said test sheet upon removal of one of said supports and said sheet carrying a test reagent;
    defecating onto said test sheet;
    removing one of said supports and flipping said sheet over and exposing the underside of said sheet;
    applying a developing solution to a portion of the underside of said sheet; and
    observing whether a portion of said sheet is dyed blue.

2. The method of claim 1 in which the reagent is guaiac.

3. The method of claim 1 in which said sheet is an absorbent paper.

4. The method of claim 1 in which said developing solution is a peroxide solution.

5. The method of claim 1 in which said sheet has openings therethrough to permit drainage of excess fluid.

6. A method for determining the presence of occult blood in fecal matter which comprises:

suspending, via a multi-support suspensing device, an absorbent test sheet from a seat of a toilet for the reception of fecal matter, said multi-support suspension device being configured to permit on-site rotation of said test sheet upon removal of one of said supports and said sheet carrying a test reagent and a hydroperoxide in dry form;

defecating onto said sheet;

removing one of said supports and flipping said sheet over to deposit the fecal matter in the bowl water and expose the underside of said sheet;

observing whether a portion of said sheet is dyed blue; and releasing said sheet from the toilet bowl and flushing.

7. The method of claim 6 in which said sheet has openings therethrough to permit drainage of excess fluid.

* * * * *